United States Patent [19]
Allais et al.

[11] 4,093,724
[45] June 6, 1978

[54] NOVEL-3-(4-QUINOLYLAMINO)-2-THIOPHENE-CARBOXYLATES

[75] Inventors: André Allais, Gagny; Jean Meier, La Varenne Saint-Hilaire; Roger Deraedt, Pavillons-sous-Bois, all of France

[73] Assignee: Roussel Uclaf, Paris, France

[21] Appl. No.: 770,304

[22] Filed: Feb. 22, 1977

[30] Foreign Application Priority Data

Feb. 23, 1976 France .................. 76 04918

[51] Int. Cl.² .................. A61K 31/495; C07D 295/14
[52] U.S. Cl. .................. 424/250; 260/287 AR; 544/363; 544/394
[58] Field of Search .................. 260/268 BQ, 288 CE, 260/287 AR; 424/250

[56] References Cited
U.S. PATENT DOCUMENTS 3,808,216  4/1974  Allais et al. .................. 260/287 AR
4,017,623  4/1977  Giudicelli et al. .................. 424/250

Primary Examiner—Paul M. Coughlan, Jr.
Attorney, Agent, or Firm—Hammond & Littell

[57] ABSTRACT

Novel 3-(4-quinolylamino)-2-thiophene-carboxylates of the formula

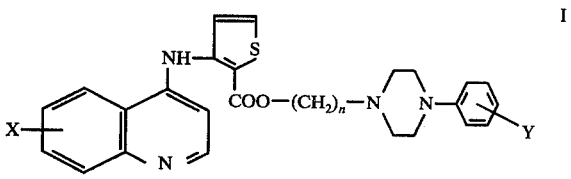

wherein X is in the 6, 7 or 8-position and is selected from the group consisting of hydrogen, halogen, —$CF_3$ and alkyl and alkoxy of 1 to 8 carbon atoms, $n$ is 2, 3, 4 or 5, Y is in the 2, 3 or 4-position and is selected from the group consisting of hydrogen, halogen, —$CF_3$ and alkyl and alkoxy of 1 to 8 carbon atoms and their non-toxic, pharmaceutically acceptable acid addition salts having analgesic activity and process and intermediates for their preparation.

20 Claims, No Drawings

NOVEL-3-(4-QUINOLYLAMINO)-2-THIOPHENE-CARBOXYLATES

STATE OF THE ART

French Pat. Nos. 2,198,736 and No. 2,228,482 describe quinoline derivatives but they contain other substituents particularly in the 4-amino group of the quinolyl group.

OBJECTS OF THE INVENTION

It is an object of the invention to provide the novel 3-(4-quinolylamino)-2-thiophene-carboxylates of formula I and their non-toxic, pharmaceutically acceptable acid addition salts.

It is a further object of the invention to provide a novel process for the preparation of the compounds of formula I and novel intermediates therefore.

It is an additional object of the invention to provide novel analgesic compositions and to a novel method of relieving pain in warm-blooded animals.

These and other objects and advantages of the invention will become obvious from the following detailed description.

THE INVENTION

The novel products of the invention are selected from the group consisting of 3-(4quinolylamino)-2-thiophene-carboxylates of the formula

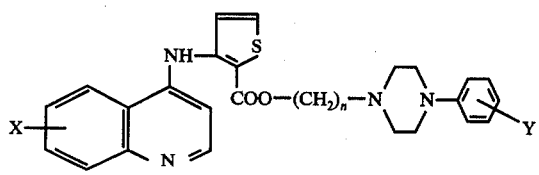

wherein X is in the 6,7 or 8-position and is selected from the group consisting of hydrogen, halogen, —$CF_3$ and alkyl and alkoxy of 1 to 8 carbon atoms, $n$ is 2,3,4 or 5, Y is in the 2,3 or 4-position and is selected from the group consisting of hydrogen, halogen, —$CF_3$ and alkyl and alkoxy of 1 to 8 carbon atoms and their non-toxic, pharmaceutically acceptable acid addition salts.

When X and Y are halogen, they are preferably chlorine, bromine or fluorine and when they are alkyl, they are preferably straight or branched chain alkyl of 1 to 6 carbon atoms such as methyl, ethyl, n-propyl, isopropyl, n-butyl, isobutyl, tert.-butyl or n-hexyl. When X and Y are alkoxy, they are preferably alkoxy of 1 to 6 carbon atoms such as methoxy, ethoxy, n-propoxy, isopropoxy, n-butoxy, isobutoxy or tert.-butoxy. $n$ is preferably 2 or 3.

The non-toxic, pharmaceutically acceptable acid addition salts are obtained with mineral acids such as hydrochloric acid, hydrobromic acid, sulfuric acid or phosphoric acid or organic carboxylic acids such as acetic acid, benzoic acid, tartaric acid, fumaric acid or maleic acid or organic sulfonic acids such as methane sulfonic acid or p-toluene sulfonic acid.

Among the preferred compounds of formula I are those wherein $n$ is 2 and their non-toxic, pharmaceutically acceptable acid addition salts, those wherein X is —$CF_3$ in the 7 or 8-position and their non-toxic, pharmaceutically acceptable acid addition salts, those wherein X is chlorine in the 7 or 8-position and their non-toxic, pharmaceutically acceptable acid addition salts, those wherein Y is —$CF_3$ and their non-toxic, pharmaceutically acceptable acid addition salts and those wherein Y is chlorine and their non-toxic, pharmaceutically acceptable acid addition salts.

Specific preferred compounds of the invention are 2-[4-(3trifluoromethylphenyl)-1-piperazinyl]-ethyl 3-[8-trifluoromethyl-4-quinolylamino]-2-thiophene-carboxylate, 2-[4-(4-chlorophenyl)-1-piperazinyl]-ethyl 3-[8-trifluoromethyl-4-quinolylamino]-2-thiophene-carboxylate, 2-[4-(3-trifluoromethylphenyl)-1-piperazinyl]-ethyl 3-(7-chloro-4-quinolylamino)-2-thiophene-carboxylate and 2-[4-(3-trifluoromethylphenyl)-1-piperazinyl]-ethyl 3-(8-chloro-4-quinolylamino)-2-thiophene-carboxylate and their non-toxic, pharmaceutically acceptable acid addition salts.

The novel process of the invention for the preparation of a compound of formula I comprises reacting a compound of the formula

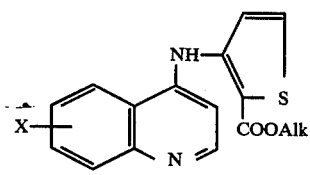

wherein X has the above definition and Alk is alkyl of 1 to 8 carbon atoms with an alcohol of the formula

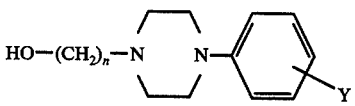

wherein $n$ and Y have the above definition to obtain a compound of formula I which may be reacted with an acid, if desired, to form the corresponding acid addition salt.

The reaction of the compounds of formulae II and III is preferably effected in the presence of an alkaline agent such as alkali metal hydride, alkali metal amide or alkali metal alcoholate in an organic solvent at a temperature of 50° to 200° C.

The compounds of formula III are generally known and may be prepared by the process described in French Pat. No. 2,141,526 and the products of formula II are generally known and may be prepared by the process of French Pat. No. 2,132,545. Methyl 3-(8-chloro-4-quinolylamino)-2-thiophene-carboxylate is a novel product.

The novel analgesic compositions of the invention are comprised of an analgesically effective amount of at least one compound of formula I and their non-toxic, pharmaceutically acceptable acid addition salts. The compositions may be in the form of tablets, coated tablets, cachets, capsules, granules, emulsions, syrups, suppositories, injectable solutions or suspensions, pomades, cremes or gels made in the usual fashion.

Examples of the pharmaceutical carriers are talc, arabic gum, lactose, starch, magnesium stearate, cacao butter, aqueous or non-aqueous vehicles, fatty bodies of animal or vegetable origin, paraffinic derivatives, glycols, preservatives, diverse wetting agents, emulsifiers or dispersants.

The compositions have a remarkable analgesic activity and may be used for the treatment of muscular, articular or nervous pains, dental pains or migraines.

The novel method of the invention for relieving pain in warm-blooded animals, including humans, comprises administering to warm-blooded animals an analgesically effective amount of at least one compound of formula I and their non-toxic, pharmaceutically acceptable acid addition salts. The compounds may be administered orally, rectally, parenterally or locally by topical application to the skin or mucous. The usual daily dose is 1 to 40 mg/kg depending on the compound and the method of administration.

In the following examples there are described several preferred embodiments to illustrate the invention. However, it should be understood that the invention is not intended to be limited to the specific embodiments.

EXAMPLE 1

2-[4-(3-trifluoromethylphenyl)-1-piperazinyl]-ethyl 3-[8-trifluoromethyl-4-quinolylamino]-2-thiophene-carboxylate dihydrochloride A mixture of 7 g of methyl 3-(8-trifluoromethyl-4-quinolylamino)-2-thiophene-carboxylate, 6.17 g of 4-(3-trifluoromethylphenyl)-1-piperazine-ethanol and 50 ml of anhydrous toluene was refluxed for an hour while passing condensed toluene through a column filled with siliporite and the mixture was cooled to 60° C. 150 mg of sodium hydride were added and the mixture was refluxed with stirring for 10 hours. The toluene was distilled and the residue was extracted with ether, washed with water and dried. The product was crystallized from methylene chloride to obtain 10.9 g of 2-[4-(3-trifluoromethylphenyl)-1-piperazinyl]-ethyl 3-(8-trifluoromethyl-4-quinolylamino)-2-thiophene-carboxylate.

The said product in 15 ml of ethanol was refluxed to obtain dissolution and 5.5 ml of an ethanolic solution of 5.17 N hydrochloric acid were added with stirring. 100 ml of ether were added to the mixture which was then iced and vacuum filtered. The precipitate was washed with ether and dried to obtain 7.3 g of the dihydrochloride salt of the said product melting at approximately 200° C

| Analysis: $C_{28}H_{26}F_6Cl_2N_4O_2S$ | | | | | | |
|---|---|---|---|---|---|---|
| | %C | %H | %F | %Cl | %N | %S |
| Calculated: | 50.38 | 3.92 | 17.08 | 10.62 | 8.39 | 4.80 |
| Found | 50.7 | 4.1 | 16.9 | 10.6 | 8.1 | 4.7 |

EXAMPLE 2

2-[4-(4-chlorophenyl)-1-piperazinyl]-ethyl 3-(8-trifluoromethyl-4-quinolylamino)-2-thiophene-carboxylate A mixture of 7.04 g of methyl 3-(8-trifluoromethyl-4-quinolylamino)-2-thiophene-carboxylate, 5.5 g of 4-(4-chlorophenyl)-1-piperazine ethanol and 50 ml of anhydrous toluene was refluxed for an hour while passing condensed toluene through a column filled with siliporite and after cooling the mixture to 60° C, 150 ml of sodium hydride were added. The mixture was refluxed with stirring for 16 hours and the toluene was distilled. The residue was extracted with methylene chloride, was washed and dried. The product was crystallized from 95% ethanol, iced and vacuum filtered. The precipitate was washed with ethanol and dried to obtain 8.6 g of 2-[4-(4-chlorophenyl)-1-piperazinyl]-ethyl 3-(8-trifluoromethyl 4-quinolylamino)-2-thiophene-carboxylate melting at 155° C.

| Analysis: $C_{27}H_{24}ClF_3N_4O_2S$ | | | | | | |
|---|---|---|---|---|---|---|
| | %C | %H | %N | %Cl | %F | %S |
| Calculated: | 57.8 | 4.31 | 9.99 | 6.32 | 10.16 | 5.72 |
| Found: | 57.8 | 4.4 | 10.0 | 6.5 | 10.3 | 5.9 |

EXAMPLE 3

2-[4-(3-trifluoromethylphenyl)-1-piperazinyl]-ethyl 3-(7-chloro-4-quinolylamino)-2-thiophene-carboxylate and its dihydrochloride A mixture of 6.37 g of methyl 3-(7-chloro-4-quinolylamino)-2-thiophene-carboxylate, 6.17 g of 4-(3-trifluoromethylphenyl)-1-piperazine-ethanol and 50 ml of anhydrous toluene was refluxed for an hour while passing condensed toluene through a column filled with siliporite and after cooling to 60° C, 150 mg of sodium hydride were added. The mixture was refluxed for 16 hours with stirring and the toluene was distilled. The residue was extracted with methylene chloride, was washed with water and dried. The product was crystallized from 20 ml of methanol and 9.5 ml of an ethanolic solution of 5.17 N hydrochloric acid were added thereto with stirring. The dihydrochloride was crystallized from a methanol-chloroform mixture and was evaporated to dryness and iced. The residue was added to 2 ml of an ethanolic solution of 5.17 N hydrochloric acid and the mixture was iced and vacuum filtered. The product was washed with ethanol and dried to obtain 9.9 g of the dihydrochloride of 2-[4-(3-trifluoromethylphenyl)-1-piperazinyl]-ethyl 3-(7-chloro-4-quinolylamino)-2-thiophene-carboxylate melting at 228° C.

The said product was dissolved in 100 ml of water and 3 ml of concentrated ammonium hydroxide were added thereto. The mixture was stirred and was vacuum filtered. The recovered precipitate was washed with water and dried to obtain 6 g of 2-[4-(3-trifluoromethylphenyl)-1-piperazinyl]-ethyl 3-(7-chloro-4-quinolylamino)-2-thiophene-carboxylate melting at 80° C.

| Analysis: $C_{27}H_{24}ClF_3N_4O_2S$ | | | | | | |
|---|---|---|---|---|---|---|
| | %C | %H | %Cl | %F | %N | %S |
| Calculated: | 57.8 | 4.31 | 6.32 | 10.16 | 9.99 | 5.71 |
| Found: | 57.5 | 4.4 | 6.5 | 10.3 | 9.9 | 5.6 |

EXAMPLE 4

2-[4-(3-trifluoromethylphenyl)-1-piperazinyl]-ethyl 3-(8-chloro-4-quinolylamino)-2thiophene-carboxylate dihydrochloride STEP A: methyl 3-(8-chloro-4-quinolylamino)-2-thiophene-carboxylate A mixture of 12 g of 4,8-dichloroquinoline, 14 g of 2-methoxycarbonyl-3-amino-thiophene, 100 ml of isopropanol and 5 ml of concentrated hydrochloric acid was refluxed during which dissolution occured followed by precipitation. The mixture was cooled to room temperature and was vacuum filtered. The product was washed and dried to obtain 18.3 g of product which was dissolved in 100 ml of isopropanol. 28 ml of triethylamine were added to the solution and the mixture was heated to 80° C for 3 hours and was poured into ice water. The mixture was vacuum filtered and the recovered precipitate was washed with water and dried to obtain 16.1 g of methyl 3-(8-chloro-4-quinolylamino)-2-thiophene-carboxylate melting at 226° C.

STEP B:
2-[4-(3-trifluoromethylphenyl)-1-piperazinyl]-ethyl 3-(8-chloro-4-quinolylamino)-2-thiophene-carboxylate dihydrochloride A mixture of 6.37 g of the product of Step A, 6.17 g of 4-[3-trifluoromethylphenyl]-1-piperazine-ethanol and 50 ml of anhydrous toluene was refluxed for an hour while passing the condensed toluene through a column filled with siliporite and after cooling to 60° C, 150 mg of sodium hydride were added thereto. The mixture was refluxed with stirring for 16 hours and the toluene was distilled. The product was extracted with methylene chloride, washed with water and dried to obtain 11.6 g of 2-[4-(3-trifluoromethylphenyl)-1-piperazinyl]-ethyl 3-(8-chloro-4-quinolylamino)-2-thiophene-carboxylate.

A solution of the said product in 20 ml of ethanol was refluxed with stirring until dissolution occured and 9.5 ml of an ethanolic solution of 5.17 N hydrochloric acid. The mixture was iced and vacuum filtered. The precipitate was washed with ethanol and dried and the product was crystallized from a mixture of 200 ml of ethanol and 2 ml of an ethanolic solution of 5.17 N hydrochloric acid to obtain 9.2 g of the dihydrochloride of 2-[4-(3-trifluoromethylphenyl)-1-piperazinyl]-ethyl 3-(8-chloro-4-quinolylamino)-2-thiophene-carboxylate melting at 245° C.

Analysis: $C_{27}H_{26}Cl_3F_3N_4O_2S$

|  | %C | %H | %N | %Cl | %F | %S |
|---|---|---|---|---|---|---|
| Calculated: | 51.15 | 4.13 | 8.83 | 16.77 | 8.99 | 5.05 |
| Found: | 51.0 | 4.4 | 8.7 | 17.1 | 9.1 | 5.0 |

PHARMACOLOGICAL DATA

Analgesic Activity

The test was based on that of Koster et al [Fed. Proc., Vol. 18 (1959) p. 412] wherein the intraperitoneal injection of acetic acid provokes in mice repeated stretching and twisting which persists for more than 6 hours and an analgesic prevents or suppresses this syndrom which is considered to be the exteriorization of a diffuse abdominal pain. A solution of 0.6% acetic acid in water containing 10% of arabic gum is used and the dose which causes the syndrom under these conditions is 0.01 ml/g or 60 mg/kg of acetic acid. The test products were orally administered 30 minutes before the intraperitoneal injection of acetic acid and the mice were fasted for 24 hours before the test.

For each dose and for the controls required in each test, groups of 5 mice were used and the stretchings were observed and counted for each mouse and added for each group, during a period of 15 minutes right after the injection. The $AD_{50}$ or dose which reduced by 50% the number of stretching as compared to the controls was determined.

TABLE

| Product of Example | $AD_{50}$ in mg/kg |
|---|---|
| 1 | 20 |
| 2 | 15 |
| 3 | 20 |

Various modifications of the products and processes of the invention may be made without departing from the spirit or scope thereof and it should be understood that the invention is intended to be limited only as defined in the appended claims.

We claim:

1. A compound selected from the group consisting of 3-(4-quinolylamino)-2-thiophene-carboxylate of the formula

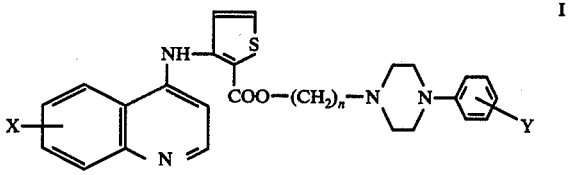

wherein X is in the 6,7 or 8-position and is selected from the group consisting of hydrogen, halogen, —$CF_3$ and alkyl and alkoxy of 1 to 8 carbon atoms, n is 2,3,4 or 5, Y is in the 2,3 or 4-position and is selected from the group consisting of hydrogen, halogen, —$CF_3$ and alkyl and alkoxy of 1 to 8 carbon atoms and their non-toxic, pharmaceutically acceptable acid addition salts.

2. A compound of claim 1 wherein n is 2.

3. A compound of claim 1 wherein X is —$CF_3$ in the 7 or 8-position.

4. A compound of claim 1 wherein X is chlorine in the 7 or 8-position.

5. A compound of claim 1 wherein Y is —$CF_3$.

6. A compound of claim 1 wherein Y is chlorine.

7. A compound of claim 1 selected from the group consisting of 2-[4-(3-trifluoromethylphenyl)-1-piperazinyl]-ethyl 3-(8-trifluoromethyl-4-quinolylamino)-2-thiophene-carboxylate and its non-toxic, pharmaceutically acceptable acid addition salts.

8. A compound of claim 1 selected from the group consisting of 2-[4-(4-chlorophenyl)-1-piperazinyl]-ethyl 3-(8-trifluoromethyl-4-quinolylamino)-2-thiophene-carboxylate and its non-toxic, pharmaceutically acceptable acid addition salts.

9. A compound of claim 1 selected from the group consisting of 2-[4-(3-trifluoromethylphenyl)-1-piperazinyl]-ethyl 3-(7-chloro-4-quinolylamino)-2-thiophene-carboxylate and its non-toxic, pharmaceutically acceptable acid addition salts.

10. A compound of claim 1 selected from the group consisting of 2-[4-(3-trifluoromethylphenyl)-1-piperazinyl]-ethyl 3-(8-chloro-4-quinolylamino)-2-thiophene-carboxylate and its non-toxic, pharmaceutically acceptable acid addition salts.

11. An analgesic composition comprising an analgesically effective amount of at least one compound of claim 1 and an inert pharmaceutical carrier.

12. A composition of claim 11 wherein the compound is selected from the group consisting of 2-[4-(3-trifluoromethylphenyl)-1-piperazinyl]-ethyl 3-(8-trifluoromethyl-4-quinolylamino)-2-thiophene-carboxylate and its non-toxic, pharmaceutically acceptable acid addition salts.

13. A composition of claim 11 wherein the compound is selected from the group consisting of 2-[4-(4-chlorophenyl)-1-piperazinyl]-ethyl 3-(8-trifluoromethyl-4-quinolylamino)-2-thiophene-carboxylate and its non-toxic, pharmaceutically acceptable acid addition salts.

14. A composition of claim 11 wherein the compound is selected from the group consisting of 2-[4-(3-trifluoromethylphenyl-1-piperazinyl]-ethyl 3-(7-chloro-4-quinolylamino)-2-thiophene-carboxylate and its non-toxic, pharmaceutically acceptable acid addition salts.

15. A composition of claim 11 wherein the compound is selected from the group consisting of 2-[4-(3-trifluoromethylphenyl)-1-piperazinyl]-ethyl 3-(8-chloro-4-quinolylamino)-2-thiophene-carboxylate and its non-toxic, pharmaceutically acceptable acid addition salts.

16. A method of relieving pain in warm-blooded animals comprising administering to warm-blooded animals in analgesically effective amount of at least one compound of claim 1.

17. A method of claim 16 wherein the compound is selected from the group consisting of 2-[4-(3-trifluoromethylphenyl)-1-piperazinyl]-ethyl 3-(8-trifluoromethyl-4-quinolylamino)-2-thiophene-carboxylate and its non-toxic, pharmaceutically acceptable acid addition salts.

18. A method of claim 16 wherein the compound is selected from the group consisting of 2-[4-(4-chlorophenyl)-1-piperazinyl]-ethyl 3-(8-trifluoromethyl-4-quinolylamino)-2-thiophene-carboxylate and its non-toxic, pharmaceutically acceptable acid addition salts.

19. A method of claim 16 wherein the compound is selected from the group consisting of 2-[4-(3-trifluoromethylphenyl)-1-piperazinyl]-ethyl 3-(7-chloro-4-quinolylamino)-2-thiophene-carboxylate and its non-toxic, pharmaceutically acceptable acid addition salts.

20. A method of claim 16 wherein the compound is selected from the group consisting of 2-[4-(3-trifluoromethylphenyl)-1-piperazinyl]-ethyl 3-(8-chloro-4-quinolylamino)-2-thiophene-carboxylate and its non-toxic, pharmaceutically acceptable acid addition salts.

* * * * *